United States Patent [19]

McVicker

[11] Patent Number: 5,368,549
[45] Date of Patent: Nov. 29, 1994

[54] METHOD FOR INJECTION-MOLDING AN ORTHOPEDIC DEVICE AND PRODUCT OF THE METHOD

[75] Inventor: Henry J. McVicker, Chatham, N.J.

[73] Assignee: Aircast, Inc., Summit, N.J.

[21] Appl. No.: 141,897

[22] Filed: Oct. 22, 1993

Related U.S. Application Data

[63] Continuation of Ser. No. 59,010, May 6, 1993, abandoned, which is a continuation of Ser. No. 665,343, Mar. 6, 1991, abandoned.

[51] Int. Cl.$^5$ .......................... A44B 18/00; A61F 5/00
[52] U.S. Cl. .......................... 602/6; 602/23; 24/452; 428/100; 264/328.1
[58] Field of Search ............ 602/5, 6, 23, 27; 428/100, 120; 425/110; 264/328.1, 328.12; 24/452

[56] References Cited

U.S. PATENT DOCUMENTS

| | | |
|---|---|---|
| 3,312,583 | 4/1967 | Rochlis . |
| 3,534,965 | 10/1970 | Harrison et al. ....... 273/DIG. 12 X |
| 3,708,833 | 1/1973 | Ribich et al. . |
| 3,927,881 | 12/1975 | Lemelson et al. ....... 273/DIG. 30 X |
| 3,955,565 | 5/1976 | Johnson, Jr. . |
| 4,165,875 | 8/1979 | Dykehouse ............. 273/DIG. 12 X |
| 4,169,303 | 10/1979 | Lemelson ............... 24/452 |
| 4,280,489 | 7/1981 | Johnson, Jr. . |
| 4,320,748 | 3/1982 | Racette et al. .......... 602/23 |
| 4,470,857 | 9/1984 | Casalou . |
| 4,563,380 | 1/1986 | Black et al. . |
| 4,673,542 | 6/1987 | Wigner et al. ........... 264/46.7 |
| 4,693,921 | 9/1987 | Billarant et al. .......... 264/46.7 X |
| 4,710,414 | 12/1987 | Northrup et al. .......... 264/46.7 X |
| 4,726,975 | 2/1988 | Hatch . |
| 4,775,310 | 10/1988 | Fischer . |
| 4,794,028 | 12/1988 | Fischer . |
| 4,802,939 | 2/1989 | Billarant et al. .......... 264/46.7 X |
| 4,814,036 | 3/1989 | Hatch . |
| 4,822,443 | 4/1989 | Dubowik . |
| 4,824,261 | 4/1989 | Provost . |
| 4,840,339 | 6/1989 | Grogan . |
| 4,842,916 | 6/1989 | Ogawa et al. .......... 428/100 |
| 4,870,725 | 10/1989 | Dubowik . |
| 4,872,243 | 10/1989 | Fischer . |
| 4,881,997 | 11/1989 | Hatch ............. 264/46.7 X |
| 4,931,344 | 6/1990 | Ogawa et al. .......... 428/100 |
| 4,933,035 | 6/1990 | Billarant et al. .......... 264/46.4 X |
| 4,981,132 | 1/1991 | Chong .................. 602/27 X |
| 4,984,339 | 1/1991 | Provost et al. . |
| 4,999,067 | 3/1991 | Erb et al. ............. 428/100 X |
| 5,007,416 | 4/1991 | Burns et al. ............. 602/27 |
| 5,031,607 | 7/1991 | Peters ................... 602/27 |
| 5,201,100 | 4/1993 | Cardinale . |

OTHER PUBLICATIONS

Two photographs of the hook-bearing portion of fastening device commercially sold under the VELCRO ® name.

*Primary Examiner*—Richard J. Apley
*Assistant Examiner*—Linda C. M. Dvorak
*Attorney, Agent, or Firm*—Jones, Day, Reavis & Pogue

[57] ABSTRACT

An injection-molded thermoplastic device having a field of injection-molded hooks integrally formed in predetermined areas on the device during the injection-molding of the device for releasable attachment to a strap with loops.

21 Claims, 3 Drawing Sheets

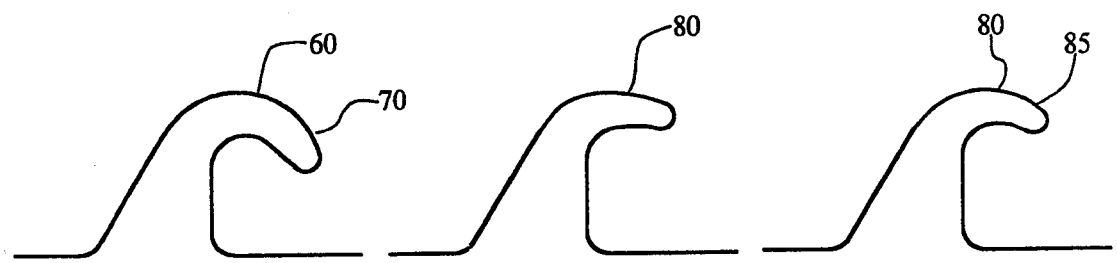
Fig.3  Fig.5  Fig.4
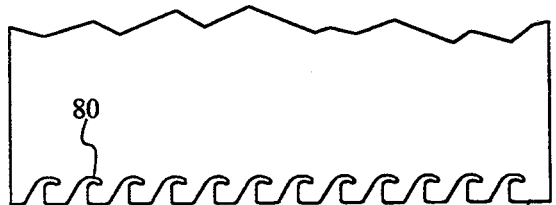
Fig.6
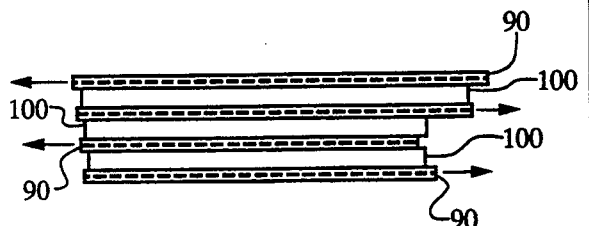
Fig.8
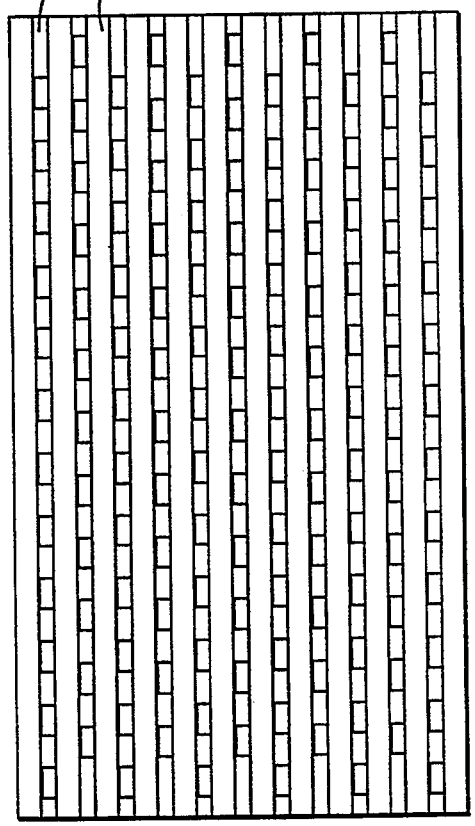
Fig.7
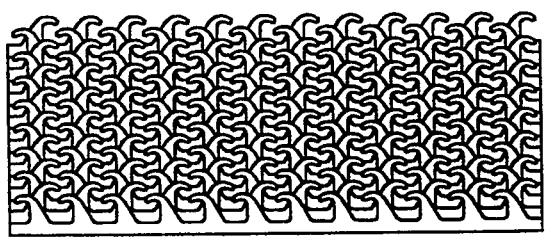
Fig.9
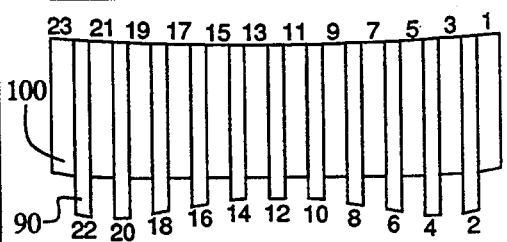
| SPACERS | | HOOKS | |
| --- | --- | --- | --- |
| NO. | H | NO. | H |
| 1 & 23 | .0014 | 2 & 22 | .0034 |
| 3 & 21 | .0053 | 4 & 20 | .0069 |
| 5 & 19 | .0083 | 6 & 18 | .0086 |
| 7 & 17 | .0106 | 8 & 16 | .0115 |
| 9 & 15 | .0121 | 10 & 14 | .0126 |
| 11 & 13 | .0129 | 12 | .013 |

METHOD FOR INJECTION-MOLDING AN ORTHOPEDIC DEVICE AND PRODUCT OF THE METHOD

This is a continuation of copending application Ser. No. 08/059,010 filed on May 6, 1993, now abandoned, which was a continuation of application Ser. No. 07/665,343 filed Mar. 6, 1991, now abandoned.

FIELD OF THE INVENTION

This invention relates to an injection-molded thermoplastic orthopedic device and a method of making same. In particular, the invention relates to a method of injection-molding a thermoplastic orthopedic device wherein at least one wall of the device has an integrally-formed field of hooks formed during the injection-molding of the orthopedic device to receive a strap loop in releasably attaching engagement in order to secure the orthopedic device generally to the circumferential contour of the lower part of the leg and ankle.

BACKGROUND OF THE INVENTION

In the management of certain injuries to the lower extremities, such as fractures of the tibia and fibula, malleolar fractures, or severe ankle sprains, it is common to completely immobilize the lower extremity (following open or closed reduction in the case of fractures) by use of the well-known molded plaster or resin cast.

After the injured extremity has become stable, however, it has been found that recovery may be effected more rapidly by gradually and progressively permitting the extremity to bear weight and undergo other permitted exercises. Thus, for example, during a second stage of management, a walking heel may be attached to a long plaster cast, or the latter replaced by a shorter unit, or by a walking cast specifically adapted to facilitate such maneuvers.

One form of walking cast commercially available under the trademark AIRCAST is described in U.S. Pat. No. 3,955,565. Additional types of orthopedic devices which permit substantially normal plantoflexion and dorsoflexion movements of the ankle but limit inversion and eversion, thus stabilizing the ankle, are also commercially available such as those described in U.S. Pat. No. 4,280,489.

In order to maintain such orthopedic devices in proper fitting engagement about the lower extremity, a pair of longitudinally-spaced, circumferentially extending fastener straps with loops, generally available under the trademark VELCRO, are usually adapted to cooperate with first and second surfaces having circumferentially-spaced fastener hooks.

The fastening material sold under the trademark VELCRO generally comprises two components. Each component has a flexible backing material having a surface thereon. One surface is comprised of the resilient hooks, while the other is comprised of a short-pile, looped fabric. As the two fastening surfaces are pressed together, the hooks releasably engage the loops, thus releasably holding the fastening materials together. The fastening surfaces are separated by pulling them apart with sufficient force to cause the resilient hooks to straighten sufficiently to come out of engagement with the loops.

Previously, VELCRO-fastener hooks were secured by conventional methods to the exterior surface of orthopedic devices. The strap loops were then adapted to matingly engage the corresponding hooks so that the strap loops could be drawn and tensioned snugly against the exterior of the orthopedic device for placement next to the lower leg or ankle. Various other methods for attaching the hooks to the orthopedic device have been utilized in the past as well. All such prior conventional methods, however, provided for the hooks to be attached to the orthopedic device after the orthopedic device was molded and formed. The present invention, however, allows the hooks to be injection-molded as an integrally-formed part of the orthopedic device.

Typically, the prior fastening hooks were manufactured attached to the surface of orthopedic devices and other devices by the use of adhesives, ultrasonic welding, stitching or through the use of continuous extrusion molding. Such former methods of manufacturing and attaching the hooks and loop fastening materials have been described in U.S. Pat. Nos. 4,814,036, 4,470,857, and 4,726,975. Improvements to the traditional, adhesive, ultrasonic welding or stitching methods have occurred through advancements in the overall process of molding the fastener material strips by extrusion molding techniques, such as those disclosed in U.S. Pat. Nos. 4,814,036, 4,563,380, 4,872,243 and 4,794,028.

All of the prior methods of attaching the hooks to various devices, including orthopedic devices, have required the use of extensive labor in the process of either cutting and applying the hooks to the previously formed orthopedic device or through the use of extrusion molding.

As the use of VELCRO-type hooks and loop fasteners has increased, however, the industry has sought less labor intensive and costly methods of manufacturing and attaching these hooks.

The present invention eliminates many of the disadvantages inherent with such prior labor-intensive and material-expensive processes of extrusion molding, adhesive and stitching by integrally forming the hooks with the orthopedic device during the injection-molding process. The present invention thereby eliminates the separate step of attaching the hooks during production.

SUMMARY OF THE INVENTION

The present invention relates to an injection-molded thermoplastic orthopedic device and method of making same. In particular, the orthopedic device includes at least one wall having an arcuate transverse cross-sectional shape sufficient to conform generally to the circumferential contour of the inner or outer side of the lower leg and ankle. The orthopedic device normally has at least one strap of material having loops therein attached to at least one wall of the orthopedic device for holding the wall against the lower leg and ankle and has a field of injection-molded hooks integrally formed on a predetermined area of at least one wall of the orthopedic device during the injection-molding process for receiving the strap loops in a releasably attached engagement.

The hooks of the present invention have a reduced radius from that of prior hooks and a changed geometry for promoting ejection during the injection-molding process, yet still maintain the desired fastening function. In the preferred embodiment of the invention, the hooks comprise spaced rows of hooks with adjacent rows of hooks facing in the opposite directions.

The thermoplastic material, preferably polypropylene, used for injection-molding the integrally-formed hooks has a memory sufficient to cause the hooks to return substantially to their original position after being removed from the mold, and yet has sufficient flexibility to allow the hooks to bend during removal from the mold and during engagement and release with the attached strap loops.

The present invention also relates to a method of forming an orthopedic device conforming generally to the lower leg and ankle and held in place by at least one strip of material having loops thereon. The method preferably comprises the steps of (1) injection-molding the orthopedic device and (2) simultaneously integrally forming a field of hooks in at least one predetermined area on the device during the injection-molding process for receiving the strap loops in releasably attaching engagement.

BRIEF DESCRIPTION OF THE DRAWINGS

These and other objects of the present invention will be more fully understood in conjunction with the detailed description and the accompanying drawings in which like numerals represent like elements and in which:

FIG. 3 is a schematic representation of the prior art hook design;

FIG. 4 is a schematic representation of the hook design in the present invention before injection-molding;

FIG. 5 is a schematic representation of the hook of the present invention after injection-molding;

FIG. 6 is a plan view of a single plate of the hooks of the present invention;

FIG. 7 is a schematic showing the layout of the alternated hook plates and spacers utilized in the insert in the injection-molding process;

FIG. 8 is a schematic representation of the end view of the mold showing the alternating layers of hook plates and spacers and the direction of the hooks in adjacent rows.

FIG. 9 is a perspective view illustrating the alternating hook direction in alternate rows;

DETAILED DESCRIPTION OF THE DRAWINGS

While the novel field of hooks disclosed hereafter could be used with any injection-molded device, it will be described herein as used with an orthopedic device, but it is to be understood that the invention is not to be so limited.

Figures 1, 2:
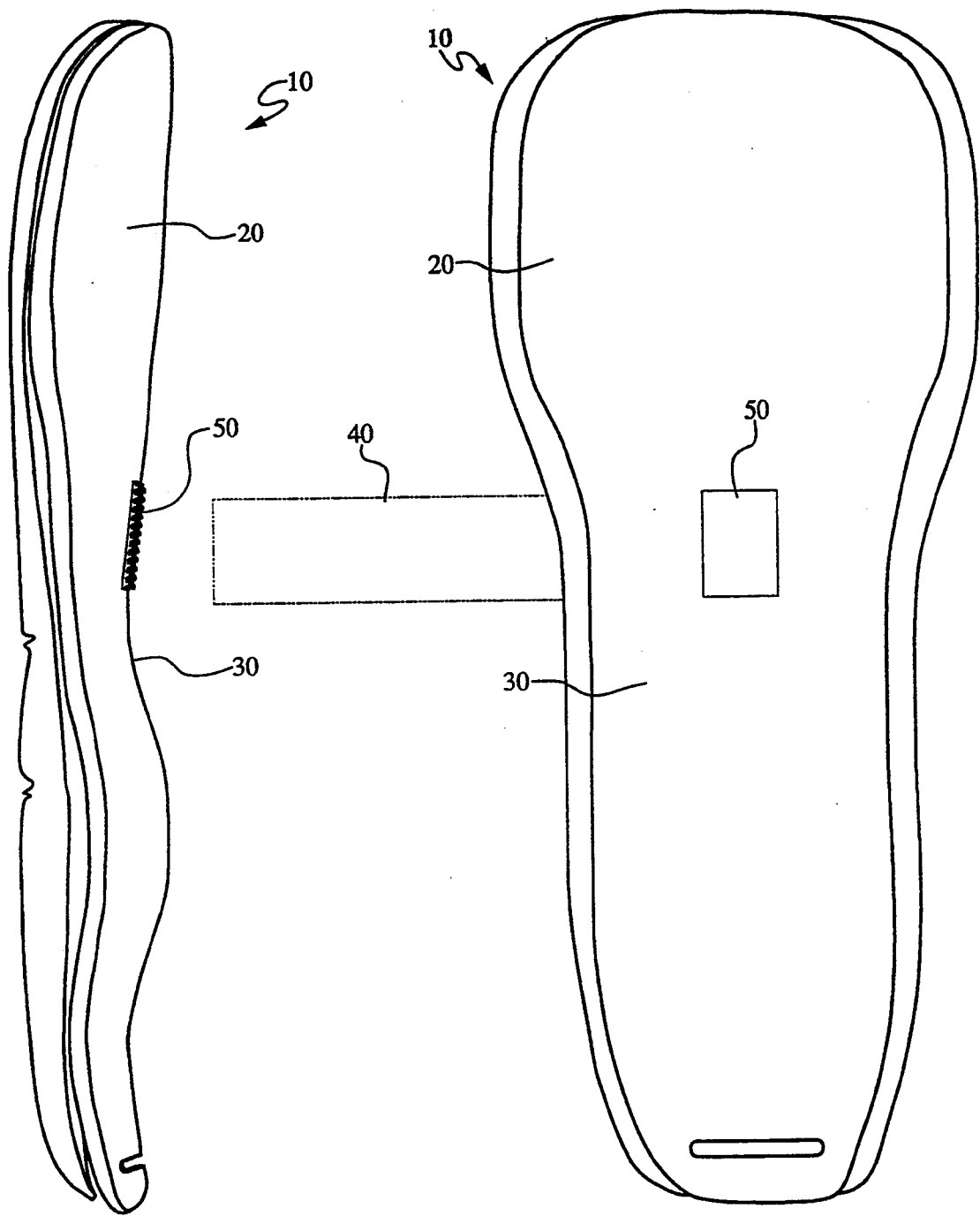
FIG. 1 is a front view of the orthopedic device.
FIG. 2 is a side view of the orthopedic device.

Turning now to FIG. 1, a front view of the orthopedic device 10 of the present invention, which, in its preferred form, comprises an ankle brace. The orthopedic device 10 is normally fitted about the lower leg and ankle of a human to provide support thereto. Orthopedic device 10 comprises a portion or wall 20 generally of a one-piece construction. The wall 20 extends longitudinally and has an arcuate transverse cross-sectional shape 30 sufficient to conform generally to the circumferential contour of the lower leg and ankle. In addition, the width of each wall 20 portion gradually tapers from a minimum, where it fits below the ankle, to a maximum at approximately the halfway point of its longitudinal extent and then extends at a substantially constant width to the remotely extending upper edge thereof.

In order to maintain the orthopedic device 10 in proper fitting engagement about the lower extremity, at least one longitudinally spaced, circumferentially extending strap loop 40 is provided. Preferably, the strap is of the well-known woven fabric construction sold under the trademark VELCRO and is adapted to cooperate with the circumferentially spaced hooks 50 having the novel type hooks thereon with the hooks being formed in predetermined areas of the orthopedic device 10 during the injection-molding process.

Although the formed field of hooks may be located in any position during the injection-molding process, as shown in FIG. 1, with respect to strap loop 40, one end of the strap loop is adapted to releasably engage the hooks 50 so that the strap loop 40 may then be drawn and tensioned snugly against the exterior of the wall 20 in a circumferential manner, to provide support to the lower leg and ankle.

Turning to FIG. 2, a side view of the orthopedic device 10 therein shows more clearly that the hooks 50 are integrally formed with the orthopedic device 10 during the injection-molding process. The hooks 50 may be integrally formed with the wall 20 at any predetermined area, including the arcuate area 30.

Turning now to FIG. 3, therein is a schematic representation of traditional VELCRO hooks 60 used in conventional attachments to prior orthopedic devices. The prior VELCRO hook 60, shown in FIG. 3, or a part of a large number of hooks on a predetermined surface area, in the past was either glued or stitched to the orthopedic device 10. Later, VELCRO became available with an adhesive backing, making it possible to peel off a liner paper from the predetermined surface area of hooks and stick it to the orthopedic shell. Additionally, such devices have been manufactured utilizing extrusion molding processes. The prior VELCRO hooks 60, as shown in FIG. 3, have a more downwardly extending area 70 than the hooks of the present invention. In addition, hook 60 has a larger radius and different geometry than that of the present invention.

FIG. 4 discloses the improved hooks 80 utilized in the orthopedic devices 10 of the present invention. The modified hooks 80 of FIG. 4 have a reduced radius and a different geometry than prior hook 60 in order to promote the ejection of the hooks during the injection-molding process yet still end up with a part that provides the desired fastening function.

Note that the exiting area 85 of hook 80 in FIG. 4 is less than that of area 70 of hook 60 in FIG. 3. It will be understood that the hook 80 of the present invention momentarily straightens after injection molding and then returns to the shape shown in FIG. 5. The hooks 80 of the present invention are made of a material that, during the injection-molding process, is supple enough to bend, yet tenacious enough to snap back and regain its molded shape. Any rigid or brittle materials would not allow the hooks 80 to bend and snap back during the injection-molding process. Such rigid or brittle materials would simply break off. On the other hand, too soft a material would lack the structural rigidity required for the hooks 80 to function as a fastener. During the injection-molding process, it is necessary for the hooks 80 to momentarily partially straighten out as the part is being pushed off the mold. In less than one second, the hooks spring back to their molded curved shape. Some deformation of the hooks 80, however, is inevitable due to the stresses occurring during ejection while the material is still hot.

In the preferred embodiment of the invention, the hooks are molded from a polypropylene. The preferred polypropylene consists of an unfilled polyester blend that is 50% homopolymer and 50% copolymer having a melt-flow index from 150° to 175° C. and a flex modulus from 130,000 to 200,000 psi. One such homopolymer with the correct physical characteristics is commercially available from Shell Corporation having part No. 5820. One such copolymer having the physical characteristics is commercially available from the Shell Corporation as part No. 7522.

FIGS. 6, 7 and 8 illustrate the plates utilized to form the hooks 80 during the injection-molding process. FIG. 6 shows that the hooks 80 are cut in each of the stacked plates 90. FIG. 6 further illustrates that a series of hooks 80 are utilized in the mold. FIG. 7 illustrates that the plates 90 containing the hooks 80 are alternated with plates 100 normally called spacers. The plates have a width of approximately 0.0156 inches and the spacers have a width of approximately 0.0312 inches. The height, h, of the spacers and plates shown in the example in FIG. 7 is illustrated in the chart associated with FIG. 7. As illustrated in FIG. 8, the hook plates 90 are separated by the spacers 100 and alternated in direction to create a more aggressive matrix than if all the hooks 80 faced the same way. Spacing of the plates 90 and 100 also allows the extraneous gases to escape during the injection-molding process. These plates may be adjusted in length as shown in FIG. 7 to produce the hooks on a curved surface such as surface 30 in FIGS. 1 and 2. FIG. 9 is a perspective view of the novel field of hooks illustrating the alternating hook direction in alternate rows of plates 90.

Figure 10:
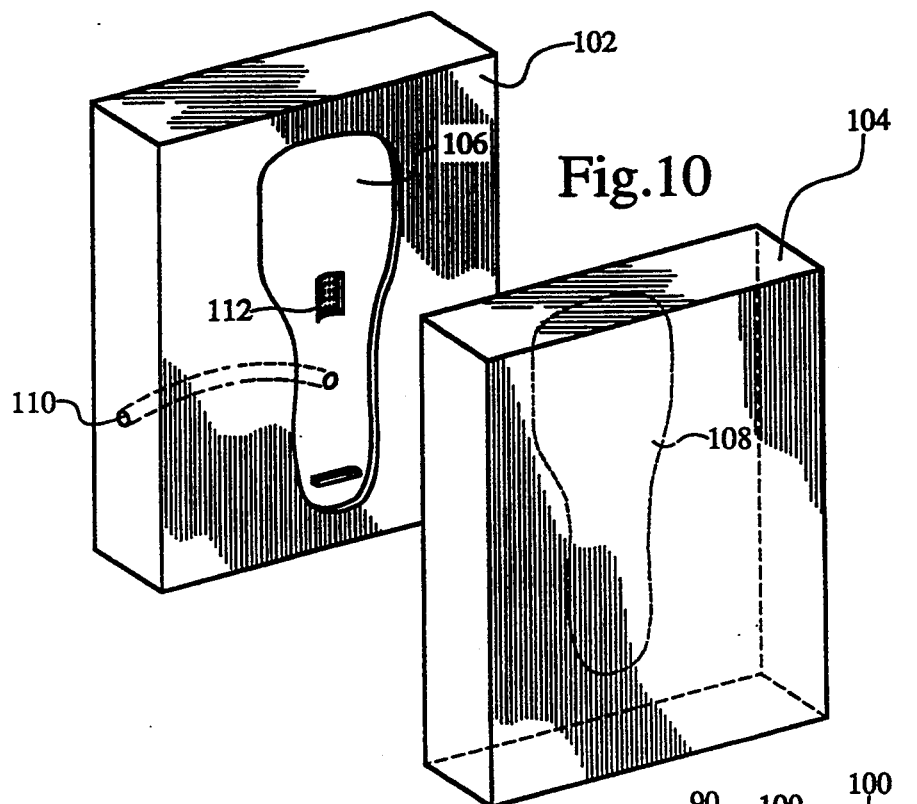
FIG. 10 is a schematic representation of a mold block for an injection-molding machine for forming the device with an integrally formed field of hooks.

A schematic representation of a mold block for an injection-molding machine is illustrated in FIG. 10. The mold block is in two sections, 102 and 104. Each of the blocks 102 and 104 has one half 106 and 108 of the shape of the orthopedic device shown in FIG. 1. The blocks 102 and 104 are brought together in liquid tight relationship in a well-known manner and the liquid plastic is injected into the cavity formed by sections 102 and 104 under pressure through orifice 110 to fill every portion of the cavity including the hook areas 80 in each plate 90.

Figure 11A:
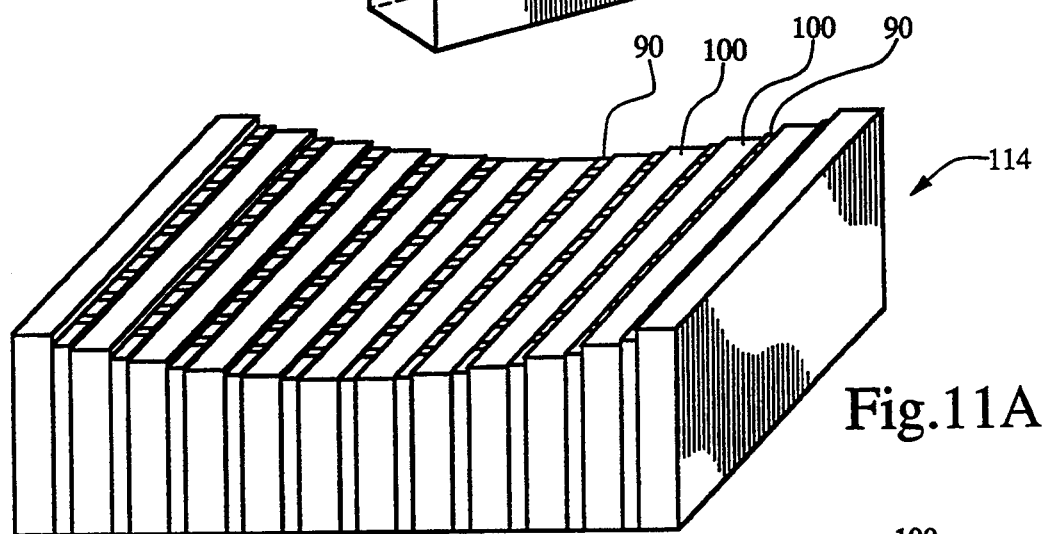
FIG. 11A and FIG. 11B are schematic representations of the insert for use in the mold block for integrally forming the field of hooks.
Figure 11B:
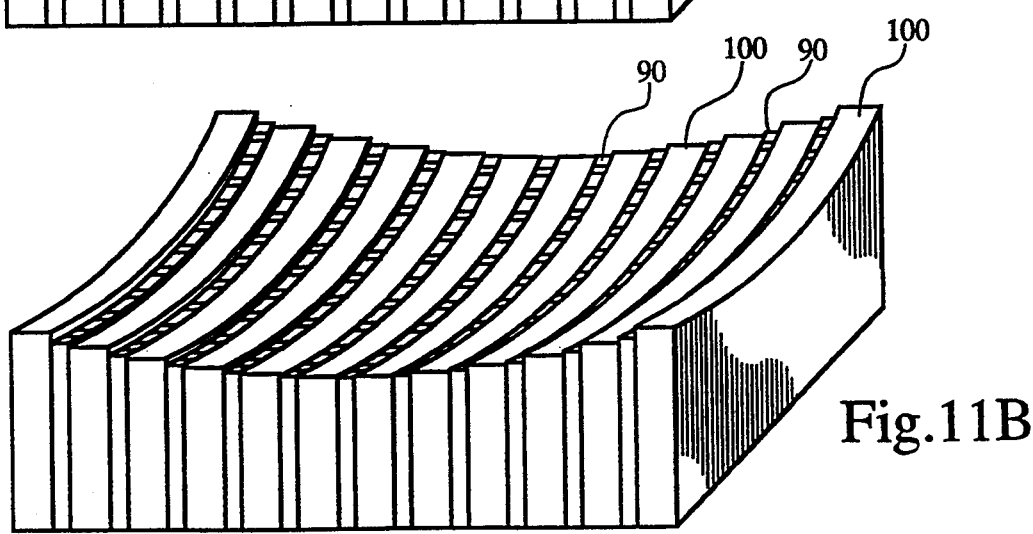

A recess 112 is formed in the mold block for receiving an insert 114, shown in FIG. 11A schematically, and which has the plates 90 and spacers 100 with the design and function described earlier. The plates may be adjusted in height and curvature with respect to each other to form any desired curved shape as shown in FIG. 11B.

Thus, there has been disclosed a novel orthopedic device and method for making the same wherein the orthopedic device has a field of injection-molded hooks integrally formed in any predetermined area on the device to receive loops on a strap for releasably engaging the straps. The field of hooks comprises spaced rows of hooks with adjacent rows of hooks facing in opposite directions. The novel hooks have a radius such that the shear force required to release the attached strap loops is substantially greater than the tension force required to release the strap loops. The thermoplastic material used for injection-molding the integrally-formed hooks, preferably polypropylene, has a memory sufficient to cause the hooks to return substantially to their original positions after being removed from the mold and sufficient flexibility to allow the hooks to bend during removal from the mold and during release of the attached strap loops. The polypropylene is an unfilled polyester blend of 50% homopolymer and 50% copolymer having a melt flow index from 150° C. to 175° C. and a flex modular from 130,000 to 200,000 psi. The novel method comprises the steps of injection-molding a plastic device and simultaneously integrally forming a field of hooks in at least one predetermined area on the device during the injection molding.

The novel apparatus for use in an injection-molding machine and disclosed herein comprises an injection mold for forming a thermoplastic device, a recess in at least one predetermined area of the mold and an insert in the recess for simultaneously and integrally forming a field of injection-molded hooks which can be used as attachment hooks.

The foregoing specification describes only the embodiment of the invention shown and/or described. Other embodiments may be articulated as well. The terms and expressions used, therefore, serve only to describe the invention by example and not to limit the invention. It is expected that others will perceive differences which, while different from the foregoing, do not depart from the scope of the invention herein described and claimed. In particular, any of the specific constructional elements described may be replaced by any other known element having equivalent function.

I claim:

1. A unitary one-piece injection-molded relatively rigid thermoplastic device having flexible hooks adapted to be releasably attachable to at least one associated cooperative loop-bearing member, the device comprising:

at least one relatively rigid wall member intended to provide a function, said wall member being injection-molded; and a field of flexible injection-molded hooks formed in their hook shape substantially simultaneously and integrally with said functional wall member during the injection-molding of the wall member on at least one predetermined area thereof, said field of hooks being structured and dimensioned for releasable attachment to the at least one associated cooperative member, said field of hooks comprising spaced rows each of one-way facing hooks, such that in each row all hooks face in the same direction and such that in at least some adjacent rows the hooks face in different directions, and said predetermined area of said field of hooks comprising substantially less than the total area of said injection-molded wall member.

2. The device in accordance with claim 1, wherein the hooks have a radius such that the shear force required to release the loops of the associated cooperative member is substantially greater than the tension force required to release the loops.

3. The device in accordance with claim 2, wherein the thermoplastic material of the device has a memory sufficient to cause the hooks to return substantially to their original shape after being removed from the mold and is of sufficient flexibility to allow the hooks to bend during removal from the mold and thereafter during the release of the loops.

4. The device in accordance with claim 3, wherein the thermoplastic material is a polypropylene.

5. The device in accordance with claim 4, wherein the polypropylene is an unfilled polyester blend of 50% homopolymer and 50% copolymer having a melt-flow index from 150° to 175° C. and a flex modulus from 130,000 to 200,000 psi.

6. The device in accordance with claim 3 wherein said wall member may have an arcuate section and wherein said field of hooks is integrally formed in a predetermined area located on any desired portion of the wall member, including the arcuate section.

7. The device as in claim 6, wherein the device is an orthopedic device.

8. The device as in claim 7, wherein said wall member has an arcuate transverse cross-sectional shape sufficient to conform generally to the circumferential contour of the inner or outer side of a lower leg and ankle; and wherein said associated cooperative loop-bearing member is releasably attachable to said field of hooks to hold the wall member against the inner or outer side of the lower leg and ankle.

9. A unitary one-piece injection molded relatively rigid thermoplastic device having hooks adapted to be releasably attachable to at least one associated cooperative loop-bearing member, the device comprising:

at least one relatively rigid wall member intended to provide a function, said wall member being injection-molded; and a field of injection-molded single tip hooks, said field having a length and a width, said field comprising hooks interspersed in both the length and the width of the field, said field of hooks being structured and dimensioned for releasable attachment to the at least one associated cooperative member, said hooks being oriented within said field such that the tips of said hooks do not all face in the same direction, such that said orientation of said hooks facilitates secure attachment of said field of hooks to said cooperative member, said field of hooks facing in different directions being formed in their hook shape substantially simultaneously and integrally with said functional wall member on at least one predetermined area thereof.

10. The device of claim 9, wherein said single tip hooks are oriented such that a substantial number of hook tips face in a first direction and a substantial number of other hook tips face in a different direction, such that said differently facing hook tips facilitate secure attachment of said field of hooks to the cooperative member.

11. The device of claim 10, wherein said hooks are arranged in rows.

12. The device of claim 11, wherein at least some hook tips in one or more rows face in a direction opposite the direction of some hook tips in an adjacent row.

13. The device of claim 12, wherein hook tips in alternating rows face in opposite directions.

14. The device of claim 9, wherein said predetermined area of said field of hooks comprises substantially less than the total area of said injection-molded wall member.

15. The device of claim 14 wherein the hooks have a radius such that the shear force required to release the loops of the associated cooperative member is substantially greater than the tension force required to release the loops.

16. The device of claim 15 wherein the thermoplastic material of the device has a memory sufficient to cause the hooks to return substantially to their original shape after being removed from the mold and is of sufficient flexibility to allow the hooks to bend during removal from the mold and thereafter during the release of the loops.

17. The device of claim 16, wherein the thermoplastic material is a polypropylene.

18. The device of claim 17, wherein the polypropylene is an unfilled polyester blend of 50% homopolymer and 50% copolymer having a melt-flow index from 150° to 175° C. and a flex modulus from 130,000 to 200,000 psi.

19. The device of claim 14, wherein said wall member may have an arcuate section and wherein said field of hooks is integrally formed in a predetermined area located on any desired portion of the wall member, including the arcuate section.

20. The device of claim 19, wherein the device is an orthopedic device.

21. The device of claim 20, wherein said wall member has an arcuate transverse cross-sectional shape sufficient to conform generally to the circumferential contour of the inner or outer side of the lower leg and ankle; and wherein said associated cooperative loop-bearing member is releasably attachable to said field of hooks to hold the wall member against the inner or outer side of the lower leg and ankle.

* * * * *